US012691044B2

(12) United States Patent
Faig et al.

(10) Patent No.: US 12,691,044 B2
(45) **Date of Patent: *Jul. 28, 2026**

(54) COSMETIC COMPOSITION HAVING STABILIZED RETINOL

(71) Applicant: L'OREAL, Paris (FR)

(72) Inventors: Jonathan James Faig, Sayreville, NJ (US); David Chan, Edison, NJ (US); Mariana Montoya, Berkeley Heights, NJ (US); Susan Halpern Chirch, Basking Ridge, NJ (US)

(73) Assignee: L'OREAL, Paris (FR)

( * ) Notice: Subject to any disclaimer, the term of this patent is extended or adjusted under 35 U.S.C. 154(b) by 933 days.

This patent is subject to a terminal disclaimer.

(21) Appl. No.: 16/916,380

(22) Filed: Jun. 30, 2020

(65) Prior Publication Data

US 2021/0401696 A1 Dec. 30, 2021

(51) Int. Cl.

| | |
|---|---|
| ***A61K 8/34*** | (2006.01) |
| ***A61K 8/06*** | (2006.01) |
| ***A61K 8/67*** | (2006.01) |
| ***A61K 8/81*** | (2006.01) |
| ***A61Q 19/08*** | (2006.01) |

(52) U.S. Cl.

CPC .............. *A61K 8/342* (2013.01); *A61K 8/062* (2013.01); *A61K 8/064* (2013.01); *A61K 8/671* (2013.01); *A61K 8/8147* (2013.01); *A61Q 19/08* (2013.01)

(58) Field of Classification Search

CPC ...................................................... A61Q 19/00

See application file for complete search history.

(56) References Cited

U.S. PATENT DOCUMENTS

| | | | | |
|---|---|---|---|---|
| 5,980,917 | A | 11/1999 | Kang et al. | |
| 6,462,025 | B2 * | 10/2002 | Vishnupad ............. | A61Q 19/00 424/78.02 |
| 8,551,465 | B2 * | 10/2013 | Bui .......................... | A61Q 1/10 424/78.02 |
| 10,137,073 | B2 | 11/2018 | De Lemos et al. | |
| 2002/0019547 | A1 | 2/2002 | Tuloup et al. | |
| 2002/0081271 | A1 | 6/2002 | Martin et al. | |
| 2002/0137795 | A1 | 9/2002 | Martin et al. | |
| 2003/0224060 | A1 | 12/2003 | Simonnet et al. | |
| 2007/0225360 | A1 | 9/2007 | Pinnell et al. | |
| 2008/0118449 | A1 | 5/2008 | Ronlan | |
| 2008/0160110 | A1 | 7/2008 | Kang et al. | |
| 2009/0286874 | A1 | 11/2009 | Pinnell et al. | |
| 2010/0284950 | A1 * | 11/2010 | Muller ..................... | A61K 8/44 424/59 |
| 2011/0020414 | A1 | 1/2011 | Kunin | |
| 2012/0283235 | A1 | 11/2012 | McCook et al. | |
| 2016/0374915 | A1 * | 12/2016 | Halpern Chirch ..... | A61K 8/466 424/60 |
| 2018/0161259 | A1 * | 6/2018 | Ha ......................... | A61K 8/891 |
| 2020/0069025 | A1 | 3/2020 | Ferebee Maher et al. | |

FOREIGN PATENT DOCUMENTS

| | | |
|---|---|---|
| ES | 2363869 T3 | 8/2011 |

OTHER PUBLICATIONS

"Tego Care 165", Evonik, 2005. (Year: 2005).*
"Eco Tween Series", Croda, 2014 (Year: 2014).*
International Search Report and Written Opinion issued on Oct. 6, 2021 for corresponding PCT Application No. PCT/US2021/039500.
Preliminary Search Report and Written Opinion issued on May 26, 2021 for corresponding French Application No. FR2009198.

* cited by examiner

*Primary Examiner* — Gina C Justice
(74) *Attorney, Agent, or Firm* — POLSINELLI PC

(57) ABSTRACT

A cosmetic composition, typically, including about 0.01 to about 3 wt. % of retinol; about 0.5 to about 10 wt. % of sodium polyacrylate; about 0.25 to about 10 wt. % of one or more nonionic emulsifier; about 3.5 to about 12 wt. % of a fatty phase, wherein the fatty phase comprises one or more fatty compound; and water, wherein all weight percentages are based on the total weight of the cosmetic composition. The cosmetic composition may be an oil-in-water emulsion.

13 Claims, No Drawings

COSMETIC COMPOSITION HAVING STABILIZED RETINOL

FIELD OF THE DISCLOSURE

The instant disclosure relates to cosmetic compositions having stabilized retinol, and particularly to cosmetic compositions having retinol that does not necessitate specialized protective packaging to protect the stabilized retinol.

BACKGROUND OF THE DISCLOSURE

Skin acts as a natural barrier between internal and external environments and therefore plays an important role in vital biological functions such as protection against mechanical and chemical injury, microorganisms, and ultraviolet damage. The health and appearance of skin, however, can deteriorate due to environmental factors, genetic makeup, nutrition, and sun exposure.

Environmental pollution conditions are fast worsening and becoming more apparent in the daily life of consumers worldwide. The damage of pollution against human skin is also becoming more and more evident. Human skin is also subjected to a variety of insults by extrinsic factors such as ultraviolet (UV) radiation, environmental pollution, wind, heat, infrared radiation, low humidity, harsh surfactants, abrasives, etc. Recent studies suggest that in addition to UV radiation, other environmental factors contribute to the development of solar lentigines, particularly air pollution. Ultimately, these factors result in visible signs of skin damage including small brown patches on the skin, especially in the elderly.

Typical skin damage includes fine lines, wrinkling, hyperpigmentation, sallowness, sagging, dark under-eye circles, puffy eyes, enlarged pores, visible dead skin, i.e., flaking, scaling, dryness, and roughness. Consumers desire to slow the gaining of skin damage and reduce the effects of aging, especially in the face and around the eyes. Radiant and clear skin appears youthful and is a sign of good health and vitality. Accordingly, there is an ongoing need for new and improved formulations that improve the health and visual appearance of skin.

SUMMARY OF THE DISCLOSURE

The present disclosure relates to cosmetic compositions having stabilized retinol, and particularly to cosmetic compositions having retinol that does not necessitate specialized protective packaging to protect the stabilized retinol. The inventors discovered that certain components in specific amounts enables cosmetic compositions with stable retinol incorporated therein, such that the cosmetic composition may be contained in non-protective packaging.

The cosmetic composition typically includes;

(a) about 0.01 to about 3 wt. % of retinol;
(b) about 0.5 to about 10 wt. % of sodium polyacrylate;
(c) about 0.25 to about 10 wt. % of one or more nonionic emulsifier;
(d) about 3.5 to about 12 wt. % of a fatty phase, wherein the fatty phase comprises one or more fatty compound; and
(e) water, wherein the cosmetic composition is an oil-in-water emulsion, and all weight percentages are based on the total weight of the cosmetic composition.

Preferably, the cosmetic compositions do not phase separate and retains at least 75 wt. % of the retinol after storage for 8 weeks at 45° C. in a light-resistant glass container.

The cosmetic composition may include about 0.3 to about 3 wt. % of sodium polyacrylate. The nonionic emulsifier may be chosen from polyglyceryl-based emulsifiers, polyol esters, glycerol ethers, oxyethylenated ethers, oxypropylenated ethers, ethylene glycol polymers, sorbitan esters, and a mixtures thereof. In some instances, the one or more nonionic emulsifier is chosen from polyglyceryl 10-stearate, polyglyceryl-3-caprate, polyglyceryl-3-diisostearate, polyglyceryl-3 methylglucose distearate, and mixtures thereof.

The cosmetic composition may comprise about 0.5 to about 5 wt. % of the fatty phase. Suitable examples of fatty compounds include fatty alcohols, fatty acids, fatty esters, oils, waxes, derivatives thereof, and mixtures thereof. In certain instances, the fatty ester may be chosen from ethoxylated fatty esters, sorbitan fatty esters, esters of stearates, esters of behenates, esters of arachidates, esters of palmitates, fatty acid esters of a sugar, and mixtures thereof. In further instances, the fatty ester may be chosen from purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, and pentaerythritol esters, and mixtures thereof. The fatty compounds may comprise isononyl isononanoate, caprylic/capric triglyceride, *Glycine soja* (soybean) oil, octyldodecanol, pentaerythritol tetraethylhexanoate, or mixtures thereof.

In some embodiments, the cosmetic composition further includes about 1 to about 35 wt. % of one or more water soluble solvent. The one or more water soluble solvent may be chosen from alkanediols, alcohols, organic solvents, polyols, and mixtures thereof. Non-limiting examples of polyols that may be incorporated into the cosmetic composition include butylene glycol, caprylyl glycol, or mixtures thereof. Non-limiting examples of alkanediols include those chosen from glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol, or a mixture thereof.

Additionally or alternatively, the cosmetic composition may further include about 0.01 to about 10 wt. % of one or more thickening agent other than sodium polyacrylate. The one or more thickening agent other than sodium polyacrylate may be chosen from chosen from acrylates, acrylates copolymers, polyacrylamide, carbomer, gums, polysaccharides, and mixtures thereof. In at least one instance, the one or more thickener other than sodium polyacrylate comprises acrylates/beheneth-25 methacrylate copolymer, methyl methacrylate crosspolymer, or a mixture thereof.

Cosmetic products of the instant disclosure typically include:

(i) a cosmetic composition in the form of an oil-in-water emulsion, the cosmetic composition comprising:
 (a) about 0.01 to about 3 wt. % of retinol,
 (b) about 0.5 to about 10 wt. % of sodium polyacrylate,
 (c) about 0.25 to about 10 wt. % of one or more nonionic emulsifier, (d) about 3.5 to about 12 wt. % of a fatty phase, wherein the fatty phase comprises at least one fatty compound, and (e) water, wherein all weight percentages are based on the total weight of the cosmetic composition, and (ii) a container containing the cosmetic composition.

The container of the cosmetic product may include a pump for dispensing the cosmetic composition. In some cases, the container contains an aluminum layer.

DETAILED DESCRIPTION OF THE DISCLOSURE

The present disclosure relates to cosmetic compositions having stabilized retinol, and particularly to cosmetic compositions having retinol that does not necessitate specialized protective packaging to protect the stabilized retinol. The inventors discovered that certain components in specific amounts enables cosmetic compositions with stable retinol incorporated therein, such that the cosmetic composition may be contained in non-protective packaging. For example, the cosmetic compositions may stabilize the retinol such that the cosmetic composition does not do not exhibit phase separation and retain at least 75 wt. % of the retinol after storage for 8 weeks at 45° C. in a light-resistant glass container.

Preferably, the cosmetic compositions do not phase separate and retain about 80 wt. % or more, about 82 wt. % or more, about 84 wt. % or more, about 86 wt. % or more, about 88 wt. % or more, about 90 wt. % or more, about 92 wt. % or more, about 94 wt. % or more, about 96 wt. % or more, 98 wt. % or more, about 99 wt. % or more, or about 99.5 wt. % or more of retinol after storage for 8 weeks at 45° C. in a light-resistant glass container. The inventors were surprised that 100 wt. % of the retinol was retained and no phase separate exhibited after storage for 8 weeks at 45° C. in a light-resistant glass container for certain embodiments of the cosmetic composition. In some cases, the cosmetic compositions exhibited no phase separation and retained about 80 wt. % or more of the retinol after storage for 8 weeks at 45° C. in a light-resistant glass container having about 5 wt. % or less, e.g., about 4 wt. % or less, about 3 wt. % or less, about 2 wt. % or less, about 1 wt. % or less, about 5000 ppm or less, about 1000 ppm or less, about 900 ppm or less, about 800 ppm or less, about 700 ppm or less, about 600 ppm or less, about 500 ppm or less, about 400 ppm or less, about 300 ppm or less, about 200 ppm or less, about 100 ppm or less, about 50 ppm or less, of oxygen in the container. In further cases, the cosmetic compositions exhibited no phase separation and retained about 80 wt. % or more of the retinol after storage for 8 weeks at 45° C. in a light-resistant glass and the cosmetic composition having 1000 ppm or less of oxygen, e.g., about 900 ppm or less, about 800 ppm or less, about 700 ppm or less, about 600 ppm or less, about 500 ppm or less, about 400 ppm or less, about 300 ppm or less, about 200 ppm or less, about 100 ppm or less, about 50 ppm or less of oxygen.

The cosmetic composition typically includes;

(a) about 0.01 to about 3 wt. % of retinol;

(b) about 0.5 to about 10 wt. % of sodium polyacrylate;

(c) about 0.25 to about 10 wt. % of one or more nonionic emulsifier; and (d) about 3.5 to about 12 wt. % of a fatty phase, wherein the fatty phase comprises one or more fatty compound; and (e) water, wherein the cosmetic composition is an oil-in-water emulsion, and all weight percentages are based on the total weight of the cosmetic composition.

Additionally, aspects of the disclosure relate to the cosmetic compositions that have a reduced fatty phase. Typically, cosmetic compositions that attempt provide stable retinol include large fatty phases with the retinol dissolved therein. The inventors discovered, however, that certain embodiments of the cosmetic compositions advantageously stabilize the retinol, such that neither protective packaging nor a large oil phase is necessary for stabilizing the retinol therein. For instance, the cosmetic compositions may include about 12 wt. % or less of a fatty phase (e.g., about 12 wt. % or less of the total amount of fatty compounds). In some cases, the cosmetic composition includes a total amount of fatty compounds of about 12 wt. % or less, about 10 wt. % or less, about 9 wt. % or less, about 8 wt. % or less, about 7 wt. % or less, about 6 wt. % or less, or about 5 wt. % or less, based on the total weight of the cosmetic composition.

The cosmetic compositions may be packaged in a container containing a pump. The pump may be a standard push pump in some cases. Preferably, the container for the cosmetic composition is a non-protective package. For example, in some instances, the cosmetic composition is contained in a container that does not include an aluminum layer or another metallic layer that acts as an oxygen barrier. Examples of non-protective packaging include standard plastic containers, such as high-density polyethelene ("HDPE"), low-density polyethelene ("LDPE"), ethylene-vinyl alcohol ("EVOH"), polyethylene terephthalate ("PET"), polyvinyl chloride ("PVC"), polypropylene ("PP"), polystyrene ("PS"), or combinations thereof. The containers may include a pump, such as a push pump or an automatic pump.

The cosmetic composition are generally formulated as an emulsion. Typically, the cosmetic compositions are formulated to be oil-in-water emulsions, with the fatty phase emulsified in the hydrophilic phase. However, in some instances, the cosmetic compositions may be formulated to have a hydrophilic phase (e.g., alcohols, glycols, polyols, etc.) emulsified in the fatty phase.

Additionally, the instant disclosure relates to methods of treating the skin comprising application of the cosmetic composition of the instant disclosure to the skin. The cosmetic compositions are additionally useful in methods for treating and/or repairing skin damage due to photoaging, and diminishing the appearance of wrinkles, dark spots, and uneven skin texture. The aforementioned methods may be non-therapeutic.

Suitable components, such as those listed below, may be included or excluded from the formulations for the cosmetic compositions depending on the specific combination of other components, the form of the cosmetic compositions, and/or the use of the formulation (e.g., a lotion, gel, cream, spray, etc.).

Retinol

The cosmetic composition includes retinol, typically, in an amount of about 0.01 to about 3 wt. %, based on the total weight of the cosmetic composition. For example, the amount of retinol present in the cosmetic composition may be from about 0.01 to about 3 wt. %, about 0.01 to about 2.5 wt. %, about 0.01 to about 2 wt. %, about 0.01 to about 1.5 wt. %, about 0.01 to about 1 wt. %, about 0.01 to about 0.75 wt. %, about 0.01 to about 0.5 wt. %; about 0.05 to about 3 wt. %, about 0.05 to about 2.5 wt. %, about 0.05 to about 2 wt. %, about 0.05 to about 1.5 wt. %, about 0.05 to about 1 wt. %, about 0.05 to about 0.75 wt. %, about 0.05 to about 0.5 wt. %; about 0.1 to about 3 wt. %, about 0.1 to about 2.5 wt. %, about 0.1 to about 2 wt. %, about 0.1 to about 1.5 wt. %, about 0.1 to about 1 wt. %, about 0.1 to about 0.75 wt. %, about 0.1 to about 0.5 wt. %; about 0.15 to about 3 wt. %, about 0.15 to about 2.5 wt. %, about 0.15 to about 2 wt. %, about 0.15 to about 1.5 wt. %, about 0.15 to about 1 wt. %, about 0.15 to about 0.75 wt. %, about 0.15 to about 0.5 wt. %; about 0.25 to about 3 wt. %, about 0.25 to about 2.5 wt. %, about 0.25 to about 2 wt. %, about 0.25 to about 1.5 wt. %, about 0.25 to about 1 wt. %, about 0.25 to about 0.75 wt. %, about 0.25 to about 0.5 wt. %, based on the total weight of the cosmetic composition.

In addition to retinol, the cosmetic composition may optionally include retinoids such as those chosen from retinoic acid, retinyl esters, and other retinol derivatives. The amount of retinoids other than retinol present in the cosmetic composition may be, e.g., about 0.01 to about 3 wt. %, about 0.01 to about 2.5 wt. %, about 0.01 to about 2 wt. %, about 0.01 to about 1.5 wt. %, about 0.01 to about 1 wt. %, about 0.01 to about 0.75 wt. %, about 0.01 to about 0.5 wt. %; about 0.05 to about 3 wt. %, about 0.05 to about 2.5 wt. %, about 0.05 to about 2 wt. %, about 0.05 to about 1.5 wt. %, about 0.05 to about 1 wt. %, about 0.05 to about 0.75 wt. %, about 0.05 to about 0.5 wt. %; about 0.1 to about 3 wt. %, about 0.1 to about 2.5 wt. %, about 0.1 to about 2 wt. %, about 0.1 to about 1.5 wt. %, about 0.1 to about 1 wt. %, about 0.1 to about 0.75 wt. %, about 0.1 to about 0.5 wt. %; about 0.15 to about 3 wt. %, about 0.15 to about 2.5 wt. %, about 0.15 to about 2 wt. %, about 0.15 to about 1.5 wt. %, about 0.15 to about 1 wt. %, about 0.15 to about 0.75 wt. %, about 0.15 to about 0.5 wt. %; about 0.25 to about 3 wt. %, about 0.25 to about 2.5 wt. %, about 0.25 to about 2 wt. %, about 0.25 to about 1.5 wt. %, about 0.25 to about 1 wt. %, about 0.25 to about 0.75 wt. %, about 0.25 to about 0.5 wt. %, based on the total weight of the cosmetic composition.

Sodium Polyacrylate(s)

The cosmetic composition includes sodium polyacrylate, typically, in an amount of about 0.5 to about 10 wt. %, based on the total weight of the cosmetic composition. For example, the amount of sodium polyacrylate present in the cosmetic composition may be from about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; about 1.25 to about 10 wt. %, about 1.25 to about 8 wt. %, about 1.25 to about 6 wt. %, about 1.25 to about 5 wt. %, about 1.25 to about 4 wt. %, about 1.25 to about 3 wt. %, about 1.25 to about 2 wt. %, including ranges and subranges therebetween, based on the total weight of the cosmetic composition.

Typically, the sodium polyacrylates may be present in the composition in a particulate or non-particulate form. When sodium polyacrylates are present in a particulate form, their mean size in the hydrated state is preferably less than or equal to 10 μm and even more preferentially less than or equal to 5 μm. Their mean size in the non-hydrated state is preferably less than or equal to 2 μm, preferably less than or equal to 1 μm.

Non-limiting examples of commercially available sodium polyacrylates include those sold under the names Octacare X100, X110 and RM100 by Avecia, those sold under the names Flocare GB300 and Flosorb 500 by SNF; those sold under the names Luquasorb 1003, Luquasorb 1010, Luquasorb 1280 and Luquasorb 1100 by BASF; those sold under the names Water Lock G400 and G430 (INCI name: Acrylamide/Sodium Acrylate Copolymer) by Grain Processing; those sold under the name Aqua Keep 10 SH NF, Aqua Keep 10 SH NFC, sodium acrylate crosspolymer-2, provided by Sumitomo Seika; and/or those sold under the names Sanfresh ST-100C, ST100MC and IM-300MC by Sanyo Chemical Industries (INCI name: Sodium Polyacrylate Starch).

Nonionic Emulsifier(s)

The cosmetic composition includes one or more nonionic emulsifier in an amount that may vary, but is typical present in the cosmetic composition in an amount of about 0.25 to about 10 wt. %, based on the total weight of the composition. In some instances, the amount of nonionic emulsifier in the cosmetic composition is about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the cosmetic composition.

Emulsifiers are, typically, used to incorporate the oil and/or fatty compounds into a hydrophilic medium, such as an aqueous medium, to form oil-in-water emulsions. In some instances, however, the emulsifiers may be used to incorporate a hydrophilic phase (e.g., aqueous medium) into an oil or fatty phase to form a water-in-oil emulsion. The cosmetic compositions includes one or more nonionic emulsifiers. Additional emulsifiers, however, can also be included (or excluded), such as amphoteric, anionic, and/or cationic emulsifiers.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof. A more exhaustive but non-limiting list of useful nonionic emulsifiers is provided later, under the heading "Nonionic Emulsifiers."

In some cases, it is preferable that cosmetic compositions containing natural oils include two or more nonionic emulsifiers. In particular, one or more nonionic emulsifier having an HLB of 10 or higher and one or more nonionic emulsifiers having an HLB of 5 or less. The total amount of these emulsifiers can be such that the final HLB of the hair-treatment composition is within +/−0.5 of the HLB of the natural oil in the cosmetic composition. This typically results in the final HLB of the emulsified natural oil in the hair-treatment composition ranging from about 6 to about 8.

Examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

Preferably, the cosmetic composition includes a nonionic emulsifier chosen from polyglyeryl-based emulsifiers, polyol esters, glycerol ethers, oxyethylenated ethers, oxypropylenated ethers, ethylene glycol polymers, sorbitan esters, polysorbate, and mixtures thereof. In some instances, the one or more nonionic emulsifier selected from polyglyceryl 10-stearate, polyglyceryl-3-caprate, polyglyceryl-3-diisostearate, polyglyceryl-3 methylglucose distearate, and mixtures thereof.

Fatty Compound(s)

The cosmetic compositions include a fatty phase comprising one or more fatty compounds. The amount of fatty phase (e.g., the total amount of fatty compounds) is typically in the range of about 3.5 to about 12 wt. %, based on the total weight of the cosmetic compositions. In some instances, the amount of fatty phase or total amount of fatty compounds is about 3.5 to about 12 wt. %, about 3.5 to about 10 wt. %, about 3.5 to about 8 wt. %, about 3.5 to about 7 wt. %, about 3.5 to about 6 wt. %, about 3.5 to about 5 wt. %; about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 12 wt. %, about 5 to about 10 wt. %, or about 5 to about 8 wt. %, about 5 to about 7 wt. %, about 5 to about 6 wt. %, including all ranges and sub-ranges therebetween, based on the total weight of the cosmetic composition.

As noted above, in some instance, the cosmetic compositions may include about 12 wt. % or less of a fatty phase (e.g., the total amount of fatty compounds). for example, the cosmetic composition may include about 12 wt. % or less, about 10 wt. % or less, about 9 wt. % or less, about 8 wt. % or less, about 7 wt. % or less, about 6 wt. % or less, or about 5 wt. % or less of a fatty phase, based on the total weight of the cosmetic composition.

Suitable fatty compounds, if present, include or may be chosen from oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, and a mixture thereof. Preferably, the fatty compound comprises a triglyceride, such as $C_{10}$-$C_{18}$ triglycerides, caprylic/capric triglycerides, or a mixture thereof. In some instances, the fatty compound comprises at least two of triglyceride, isononyl isononanoate, and *Glycine soja* (soybean) oil/ *Glycine soja* oil.

Fatty Alcohols

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arachidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

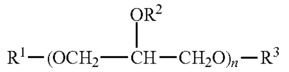

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Wax(es)

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Oil(s)

In some instances, the fatty compounds may include or be chosen from one or more oil(s). Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelargonate; and triesters, such as glyceryl trioctanoate. Non-limiting examples of oils that may, optionally, be included in the cosmetic compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

The cosmetic compositions may include an oils comprising low $O_2$ permeable oils (e.g., oils having an $O_2$ permeability of 0.3% or less); medium $O_2$ permeable oils (e.g., oils having an $O_2$ permeability of 0.3% to 0.4%); and/or higher $O_2$ permeable oils (e.g., oils having an $O_2$ permeability of greater than 0.4%). In some cases, the cosmetic composition includes an amount of low $O_2$ permeable oils of about 50 wt. % or more, about 60 wt. % or more, about 70 wt. % or more, about 80 wt. % or more, about 85 wt. % or more, or about 90 wt. % or more, based on the total weight of the oils and/or oil phase. The cosmetic composition may include an amount of medium $O_2$ permeable oils of about 50 wt. % or less, about 40 wt. % or less, about 30 wt. % or less, about 20 wt. % or less, about 10 wt. % or less, about 5 wt. % or less. Additionally or alternatively, the cosmetic composition may include an amount of higher $O_2$ permeable oils of about 30 wt. % or less, about 20 wt. % or less, about 10 wt. % or less, about 5 wt. % or less.

Water-Soluble Solvent(s)

The cosmetic compositions may include one or more water-soluble solvents. The amount of water-soluble solvents in the cosmetic composition, if present, may range from about 1 to about 35 wt. %, based on the total weight of the cosmetic composition. For example, the cosmetic composition may include water-soluble solvents in an amount of about 1 to about 35 wt. %, about 1 to about 30 wt. %, about 1 to about 25 wt. %, about 1 to about 20 wt. %, about 1 to about 18 wt. %, about 1 to about 16 wt. %, about 1 to about 14 wt. %, about 1 to about 12 wt. %, about 1 to about 10 wt. %; about 5 to about 35 wt. %, about 5 to about 30 wt. %, about 5 to about 25 wt. %, about 5 to about 20 wt. %, about 5 to about 18 wt. %, about 5 to about 16 wt. %, about 5 to about 14 wt. %, about 5 to about 12 wt. %, about 5 to about 10 wt. %; about 10 to about 35 wt. %, about 10 to about 30 wt. %, about 10 to about 25 wt. %, about 10 to about 20 wt. %, about 10 to about 18 wt. %, about 10 to about 16 wt. %, about 10 to about 14 wt. %; about 12 to about 35 wt. %, about 12 to about 30 wt. %, about 12 to about 25 wt. %, about 12 to about 20 wt. %, about 12 to about 18 wt. %, about 12 to about 16 wt. %; about 14 to about 35 wt. %, about 14 to about 30 wt. %, about 14 to about 25 wt. %, about 14 to about 20 wt. %, about 14 to about 18 wt. %; about 16 to about 35 wt. %, about 16 to about 30 wt. %, about 16 to about 25 wt. %, about 16 to about 20 wt. %; about 18 to about 35 wt. %, about 18 to about 30 wt. %, about 18 to about 25 wt. %, about 18 to about 20 wt. %, including ranges and subranges thereof, based on the total weight of the cosmetic composition.

The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90%. Non-limiting examples of water-soluble solvents include, for example, glycerin, alcohols (for example, $C_{1-30}$, $C_{1-15}$, $C_{1-10}$, or $C_{1-4}$ alcohols), organic solvents, polyols (polyhydric alcohols), glycols (e.g., butylene glycol, caprylyl glycol, etc.), and a mixture thereof.

In some cases, the water-soluble solvent is a monoalcohol. Non-limiting examples of monoalcohols include ethanol, propanol, butanol, pentanol, hexanol, isopropyl alcohol, cyclohexanol, isobutyl alcohol, 2-methyl-2-butanol (2-methylbutan-2-ol), and a mixture thereof. In some instances, the monoalcohols comprise or are chosen from ethanol, propanol, butanol, pentanol, an isomer thereof, or a combination thereof. In further instances, the one or more monoalcohol(s) includes or consists of ethanol.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. The water-soluble solvents may be organic solvents that can be volatile or non-volatile compounds.

Further non-limiting examples of water-soluble solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. The term "polyol" should be understood as meaning, within the meaning of the present disclosure, an organic molecule comprising at least two free hydroxyl groups. The polyols of the cosmetic composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Non-limiting examples of polyols that may, optionally, be included in the cosmetic composition include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof. The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol.

In some cases, the polyol comprises glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

Thickening Agent(s) Other than Sodium Polyacrylate

The cosmetic compositions described herein may, optionally, include a thickening agent other than sodium polyacrylate. The thickening agent other than sodium polyacrylate may be in an amount of about 0.01 to about 10 wt. %, about 0.01 wt. % to about 9 wt. %, about 0.01 wt. % to about 8 wt. %, about 0.01 wt. % to about 7 wt. %, about 0.01 wt. % to about 6 wt. %, about 0.01 wt. % to about 5 wt. %, about 0.01 wt. % to about 4 wt. %, about 0.01 wt. % to about 3 wt. %, about 0.01 wt. % to about 2 wt. %, about 0.01 wt. % to about 1 wt. %; about 0.1 to about 10 wt. %, about 0.1 wt. % to about 9 wt. %, about 0.1 wt. % to about 8 wt. %, about 0.1 wt. % to about 7 wt. %, about 0.1 wt. % to about 6 wt. %, about 0.1 wt. % to about 5 wt. %, about 0.1 wt. % to about 4 wt. %, about 0.1 wt. % to about 3 wt. %, about 0.1 wt. % to about 2 wt. %, about 0.1 wt. % to about 1 wt. %; about 0.2 to about 10 wt. %, about 0.2 wt. % to about 9 wt. %, about 0.2 wt. % to about 8 wt. %, about 0.2 wt. % to about 7 wt. %, about 0.2 wt. % to about 6 wt. %, about 0.2 wt. % to about 5 wt. %, about 0.2 wt. % to about 4 wt. %, about 0.2 wt. % to about 3 wt. %, about 0.2 wt. % to about 2 wt. %, about 0.2 wt. % to about 1 wt. %; about 0.3 to about 10 wt. %, about 0.3 wt. % to about 9 wt. %, about 0.3 wt. % to about 8 wt. %, about 0.3 wt. % to about 7 wt. %, about 0.3 wt. % to about 6 wt. %, about 0.3 wt. % to about 5 wt. %, about 0.3 wt. % to about 4 wt. %, about 0.3 wt. % to about 3 wt. %, about 0.3 wt. % to about 2 wt. %, about 0.3 wt. % to about 1 wt. %, including ranges and subranges thereof, based on the total weight of the cosmetic composition. Further, the amount of thickening agent may be from 0.1, 0.2, 0.3, 0.4, 0.5, 0.6, 0.7, 0.8, 0.9, 1.0, or 1.5 wt. % to 2, 3, 4, 5, 6, 7, 8, 9, or 10 wt. %, including ranges and subranges thereof, based on the total weight of the cosmetic composition.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickening agent other than sodium polyacrylate may be dispersed/dissolved in an aqueous solvent that is soluble in water, e.g., ethyl alcohol when it is dispersed/dissolved in water.

Thickening agents may be referred to as "thickeners" or "viscosity modifying agents." Thickening agents are typically included to increase the viscosity of the compositions. Nonetheless, in some instances, certain thickening agents provide additional, surprising benefits to the compositions. Non-limiting examples of thickening agents include polyacrylate crosspolymers (other than sodium polyacrylate) or crosslinked polyacrylate polymers (other than crosslinked sodium polyacrylate), cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Suitable thickeners other than sodium polyacrylate may be found in U.S. patent application Ser. No. 16/731,654, which is incorporated herein, in its entirety for all purposes.

The thickening agents other than sodium polyacrylate may be chosen from xanthan gum, guar gum, biosaccharide gum, cellulose, acacia seneca gum, *sclerotium* gum, agarose, pechtin, gellan gum, hyaluronic acid. Additionally, the thickening agents other than sodium polyacrylate may include polymeric thickeners selected from the group consisting of ammonium polyacryloyldimethyl taurate, ammonium acryloyldimethyltaurate/VP copolymer, acrylates copolymers, polyacrylamide, carbomer, and acrylates/C10-30 alkyl acrylate crosspolymer.

Particular types of thickening agents that may be mentioned include the following:

Carboxylic Acid or Carboxylate Based Homopolymer or Co-Polymer, which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Polyquaternium Compounds

Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof. In some instances, the cosmetic compositions include polyquaternium-10, polyquaternium-11, polyquaternium-67, or a mixture thereof.

Celluloses

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC). In some instances, the cosmetic compositions include one or more cellulose thickeners (e.g., microcrystalline cellulose, carboxymethylcellulose, hydroxymethylcellulose, and hydroxypropylcellulose).

Polyvinylpyrrolidone (PVP) and Co-Polymers

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commercially available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octaolate, and mixed esters, such as sucrose palmitate/stearate, and mixtures thereof.

Polyglyceryl Esters

Non-limiting polyglycerol esters of fatty acids (polyglyceryl esters) include those of the following formula:

$$R^1-(OCH_2-\overset{\displaystyle OR^2 \atop |}{CH}-CH_2O)_n-R^3$$

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

C8-24 Hydroxyl Substituted Aliphatic Acid and C8-24 Conjugated Aliphatic Acid

Non-limiting examples include conjugated linoleic acid, cis-parinaric acid, trans-7-octadecenoic acid, cis-5,8,11,14,17-eicosapentaenoic acid, cis-4,7,10,13,16,19-docosahexanoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranoic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof.

Gums

Non-limiting examples of gums include gum arabic, tragacanth gum, karaya gum, guar gum, gellan gum, tara gum, locust bean gum, tamarind gum, xanthan gum, locust bean gum, seneca gum, *sclerotium* gum, etc.

Skin Active Agents

The cosmetic compositions may, optionally, include one or more skin active agents, such as anti-aging agent, anti-wrinkle actives, anti-oxidants, humectants, moisturizing ingredients, depigmenting agents, and/or agents for treating oily skin etc. The skin active agents may be included in the cosmetic composition in an amount ranging from greater than zero to about to about 10 wt. %, based on the total weight of the composition. For example, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; from about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; from about 0.1 to about 10 wt. %, about 0.1 to about 5 wt. %, about 0.1 to about 2.5 wt. %, about 0.1 to about 1 wt. %, about 0.1 to about 0.5 wt. %; from about 1 to about 10 wt. %, about 1 to about 8 wt. %, about 1 to about 6 wt. %, about 1 to about 5 wt. %, about 1 to about 4 wt. %, about 1 to about 3 wt. %; from about 2 to about 10 wt. %, about 2 to about 8 wt. %, about 2 to about 6 wt. %, about 2 to about 5 wt. %, about 2 to about 4 wt. %; from about 3 to about 10 wt. %, about 3 to about 8 wt. %, about 3 to about 6 wt. %, about 3 to about 5 wt. %; from about 4 to about 10 wt. %, about 4 to about 8 wt. %, about 4 to about 6 wt. %, including ranges and subranges therebetween, based on the total weight of the cosmetic composition.

A non-limiting discussion of skin active agents that may, in some cases, be included in the cosmetic composition is provided below:

Humectants and/or Moisturizing Ingredients

Examples of humectants and/or moisturizing ingredients include glycerol and its derivatives, urea and its derivatives, especially Hydrovance marketed by National Starch, lactic acid, hyaluronic acid, AHA, BHA, sodium pidolate, xylitol, serine, sodium lactate, ectoine and its derivatives, chitosan and its derivatives, collagen, plankton, an extract of *Imperata cylindra* sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract *Prophyridium cruentum* enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting Agents

Depigmenting agents that may be incorporated in the cosmetic composition include those chosen from alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, certain compounds derived from plants such as chamomile, bearberry, the aloe family (*vera, ferox, bardensis*), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

Anti-Wrinkle Active

The cosmetic composition may include one or more anti-wrinkle actives. The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinoids other than retinol (as discussed above), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *Laminaria*, bacterial extracts, the sapogenins such as diosgenin and extracts of *Dioscorea* plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof. In at least one case, the cosmetic composition includes adenosine derivatives, such as non-phosphate derivatives of adenosine, such as in particular the 2'-deoxyadenosine, 2',3'-adenosine isopropylidene; the toyocamycin, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethylamino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

Skin Active Agent for Oily Skin

The cosmetic composition may, optionally, include a skin active agent that addresses oily skin. These agents can be sebo-regulating or antiseborrhoeic agents capable of regulating the activity of sebaceous glands. Exemplary skin active agents for addressing oily skin include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate—derivatives particularly copper and copper pidolate as Cuivridone Solabia—extracts from plants of *Arnica montana, Cinchona succirubra, Eugenia caryophyllata, Humulus lupulus, Hypericum perforatum*, Mentha pipenta 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—*Phellodendron* extracts such as those sold under the name *Phellodendron* extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm— mixtures of extracts of willowherb, of *Terminalia chebula*, nasturtium and of bioavailable zinc (microalgae), such as that sold under the name Seborilys Green Tech—extracts of *Pygeum afrianum* such as that sold under the name *Pygeum afrianum* sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *Laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of *cinchona* bark *succirubra* such as that sold under the name Red Bark HS by Alban Muller—extracts of *Quillaja saponaria* such as that sold under the name 15 Panama wood HS by Alban Muller—*Glycine* grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decanediol such as that sold under the name Acnacidol BG by Vincience and mixtures thereof.

Antioxidants

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, *Emblica officinalis*, and bioflavonoids from rose hip and citrus may be used including water soluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

Other antioxidants include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ-tocotrienol, d-delta-tocotrienol) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

In addition, carotenoids, particularly the xanthophyll type, are also useful antioxidants that can be used. The xanthophyll type carotenoids include molecules, such as lutein, canthaxanthin, cryptoxanthin, zeaxanthin and astaxanthin. Xanthophylls protect compounds, such as vitamin A, vitamin E, and other carotenoids.

Flavonoids

The active agent may be an antioxidant selected from the group of flavonoids. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadendrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcumin, bis-Desmethoxycurcumin, Tetrahydrocurcumin, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (*Sesamum indicum*) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

Mattifyinq Agent(s)

The cosmetic compositions of the instant disclosure may include a mattifying agent. The amount of mattifying agent in the cosmetic composition may be, e.g., about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the cosmetic composition.

Mattifying agents (also referred to as "mattifying fillers") refer to material that gives the complexion more transparency and a hazy effect and provides skin with a natural and desirable appearance, without conferring on it a greasy, gleaming and shiny appearance. To do this, these materials are often absorbent fillers such as talc, silica, kaolin or fillers having light scattering optical properties, which properties are known under the name "soft focus" effect. In addition to reducing the shine or oiliness, mattifying agents can contribute to the overall texture and thickness of a cosmetic composition. Mattifying agents are often (but not always) particulate material or powders.

Cosmetic compositions containing mattifying agents may be characterized by means of the following protocol. The test composition is spread out at a rate of 2 mg/$cm^2$ on a contrast card (Prufkarte type 24/5-250 $cm^2$ sold by the company Erichsen) using a mechanical film spreader. The composition is then dried overnight at a temperature of 37° C. prior to measurement of its reflection using a goniore-flectometer sold by the company Micromodule. The intensity reflected specularly at 30° (R) and scattered at 90° (D) are successively measured. The result obtained is the ratio R between the specular reflection and the diffuse reflection. The value of R is proportionately smaller the greater the mattifying effect afforded by the filler. A value of R of less than or equal to 2 generally indicates a mattifying effect. The mattifying agents according to the instant disclosure include those which, preferably at a content of 5% in a cosmetic composition, give a value of R of less than 1.5 and preferably less than 1.

Non-limiting examples of mattifying agents include: silicas, clays, silicate derivatives, hydrophobic silica aerogel particles, porous silica microparticles, for instance the Silica Beads SB150 and SB700 from Miyoshi with a mean size of 5 microns; the Sunsphere Series-H products from Asahi Glass, for instance Sunsphere H33, H51 and H53 with respective sizes of 3, 5 and 5 μm, polytetrafluoroethylene powders, for instance PTFE Ceridust 9205F from Clariant, with a mean size of 8 microns, silicone resin powders, for instance the silicone resin Tospearl 145A from GE Silicone, with a mean size of 4.5 microns, hollow hemispherical silicone particles, for instance NLK 500, NLK 506 and NLK 510 from Takemoto Oil and Fat, acrylic copolymer powders, especially of polymethyl(meth)acrylate, for instance the PMMA particles Jurymer MBI from Nihon Junyoki, with a mean size of 8 microns, the hollow PMMA spheres sold under the name Covabead LH 85 by the company Wackher, and the vinylidene chloride/acrylonitrile/methylene methacrylate expanded microspheres sold under the name Expancel; wax powders, for instance the paraffin wax particles MicroEase 114S from MicroPowders, with a mean size of 7 microns, polyethylene powders, especially comprising at least one ethylene/acrylic acid copolymer, and in particular consisting of ethylene/acrylic acid copolymers, for instance the Flobeads EA 209 particles from Sumitomo (with a mean size of 10 microns), crosslinked elastomeric organopolysiloxane powders coated with silicone resin, especially with silsesquioxane resin, as described, for example, in U.S. Pat. No. 5,538,793. Such elastomeric powders are sold under the names KSP-100, KSP-101, KSP-102, KSP-103, KSP-104 and KSP-105 by the company Shin-Etsu, polyamide (Nylon®) powders, for instance Nylon 12 particles of the Orgasol type from Atofina, with a mean size of 10 microns, powders of polymethyl methacrylate (PMMA) type, talc, silica/$TiO_2$ or silica/zinc oxide composites, styrene/acrylic copolymer powders, and mixtures thereof.

Among clays, mention may be made of clays of the smectite family, such as laponite, of the kaolinite family, such as kaolinite, dickite or nacrite, optionally modified clays of the halloysite, dombassite, antigorite, benthierine or pyrophyllite family, montmorillonites, beidellite, vermiculites, talc, stevensite, hectorites, saponites, chlorites, sepiolite and illite.

Clays include products that are described, for example, in the publication Mineralogie des argiles [Mineralogy of Clays], S. Caillere, S. Henin, M. Rautureau, 2nd Edition 1982, Masson, which is incorporated herein by reference in its entirety. Natural clay is a sedimentary rock in large part composed of specific minerals, silicates, generally, of aluminum. Kaolin is a natural clay. The clays may also be synthetic. Clays can also be chemically modified by various compounds, such as acrylic acids, polysaccharides (for example carboxymethylcellulose) or organic cations. In some instances, the cosmetic compositions of the instant disclosure includes a clay selected from the group consisting of kaolinite, montmorillonites, saponites, laponites, hectorites (including disteardimonium hectorite), and illites.

Silica derivatives that may be mentioned include silica powders, for instance the porous silica microspheres sold under the name SILICA BEADS SB-700 sold by the company Miyoshi, the products SUNSPHERE H51, SUNSPHERE H33 and SUNSPHERE H53 sold by the company Asahi Glass; the polydimethylsiloxane-coated amorphous silica microspheres sold under the name SA SUNSPHERE H-33 and SA SUNSPHERE H-53 sold by the company Asahi Glass; silica microbeads such as those sold under the name SB150 by the company Miyoshi.

In some instances, the cosmetic compositions include one or more mattifying agents selected from the group consisting of methyl methacrylate/glycol dimethacrylate crosspolymer, vinyl dimethicone/methicone silsesquioxane crosspolymer, methyl methacrylate crosspolymer, nylon-12, polyamides, polyethylene, talc, titanium dioxide, silica, aluminum starch octenylsuccinate, clays (such as hectorite clays including distearidimonium hectorite), silicas, polymethylsilsesquioxane, and a mixture thereof. Preferably, the mattifying agent, if present, is aluminum starch octenylsuccinate.

Silicone(s)

The cosmetic compositions described herein may comprise one or more silicone. The amount of silicone(s) in the composition may vary from, e.g., about 0.1 to about 20 wt. %, based on the total weight of the composition. In some instances, the total amount of silicone is from about 0.01 to about 20 wt. %, from about 0.01 to about 15 wt. %, about 0.01 to about 10 wt. %, about 0.01 to about 8 wt. %, about 0.01 to about 6 wt. %, about 0.01 to about 4 wt. %, about 0.01 to about 2 wt. %, about 0.01 to about 1 wt. %; from about 0.1 to about 20 wt. %, from about 0.1 to about 15 wt. %, about 0.1 to about 10 wt. %, about 0.1 to about 8 wt. %, about 0.1 to about 6 wt. %, about 0.1 to about 4 wt. %, about 0.1 to about 2 wt. %, about 0.1 to about 1 wt. %; from about 0.25 to about 20 wt. %, about 0.25 to about 15 wt. %, about 0.25 to about 10 wt. %, about 0.25 to about 8 wt. %, about 0.25 to 6 wt. %, or about 0.25 to 5 wt. %, about 0.25 to about 4 wt. %, about 0.25 to about 2 wt. %, about 0.25 to about 1 wt. %; from about 0.5 to about 20 wt. %, about 0.5 to about 15 wt. %, about 0.5 to about 10 wt. %, about 0.5 to about 8 wt. %, about 0.5 to 6 wt. %, or about 0.5 to 5 wt. %, about 0.5 to about 4 wt. %, about 0.5 to about 2 wt. %, about 0.5 to about 1 wt. %, including ranges and sub-ranges therebetween, based on the total weight of the cosmetic composition.

Non-limiting examples of silicones include dimethicone, cyclomethicone, polysilicone-11, phenyl trimethicone, trimethylsilylamodimethicone, and stearoxytrimethylsilane. Typically, the one or more silicone is a non-volatile silicon oil. In some embodiments, the silicone is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates.

Other examples of silicone that may be mentioned include volatile linear or cyclic silicones, such as those with a viscosity 8 centistokes (8×106 m2/s) and/or containing from 2 to 7 silicon atoms. These silicones optionally comprise alkyl or alkoxy groups containing from 1 to 10 carbon atoms. Non-limiting examples of volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, or mixtures thereof.

pH Adjuster(s)

The cosmetic composition may include one or more pH adjusters to increase or decrease the overall pH of the cosmetic composition. For example, one or more acids may be included to decrease the pH of the cosmetic composition. Examples of suitable acids for decreasing the pH of the cosmetic composition include, but are not limited to, citric acid, acetic acid, and the like. The cosmetic composition may include one or more bases, such as sodium hydroxide, potassium hydroxide and the like, to decrease the pH of the cosmetic composition. Additional or alternative acids and bases that are suitable for adjusting the pH of the cosmetic composition are readily known to one of ordinary skill in the art.

The cosmetic composition may, desirably, have a pH of about 4 to about 7, preferably about 4.5 to about 6.5 or about 5.5 to about 6.5. In one instance, the pH of the cosmetic composition is 6 or about 6. The amount of the pH adjuster in the cosmetic composition may be based on the desired pH of the final cosmetic composition and/or product. For example, the total amount of the pH adjuster may range from about 0.05 to about 20 wt. %, based on the total weight of the composition. In some instances, the total amount of pH adjuster is from about 0.05 to about 15 wt. %, about 0.5 to about 10 wt. %, about 1 to about 5 wt. %, about 1.5 to about 4 wt. %, or about 2.0 to about 3 wt. %, including ranges and sub-ranges therebetween, based on the total weight of the composition.

Water

The total amount of water in the cosmetic composition can vary, but is typically about 50 to about 95 wt. %, based on the total weight of the cosmetic composition. In some instances, total amount of water is about 50 to about 90 wt. %, about 50 to about 85 wt. %, about 50 to about 80 wt. %; about 55 to about 95 wt. %, about 55 to about 90 wt. %, about 55 to about 85 wt. %, about 55 to about 80 wt. %; about 60 to about 95 wt. %, about 60 to about 90 wt. %, about 60 to about 85 wt. %, about 60 to about 80 wt. %; about 65 to about 95 wt. %, about 65 to about 90 wt. %, about 65 to about 85 wt. %, or about 65 to about 80 wt. %; about 70 to about 95 wt. %, about 70 to about 90 wt. %, about 70 to about 85 wt. %, about 70 to about 80 wt. %, including ranges and subranges therebetween, based on the total weight of the cosmetic composition.

Methods of Production

The instant disclosure also relates to methods or processes for making/manufacturing the cosmetic compositions described herein. It also encompasses the products prepared by these methods or processes. Typically, a process for making the cosmetic compositions of the instant disclosure comprises the formation of an oil phase and the formation of a separate aqueous phase (containing water), both phases are heated and combined while warm. Each phase may be heated to the same temperature or may be heated to different temperatures.

The thickening agents may be added to the aqueous phase of the cosmetic compositions. In some instances, however, the one or more emulsifiers and/or the thicken agents are added to the oil phase. Additionally or alternatively, thickening agents may be added post-emulsification—for instance, ammonium polyacryloydldimethyl taurate may be added post-emulsification.

After combining the oil phase and the aqueous phase to form an emulsion, the composition is typically allowed to cool. Additional components may be added during the time of emulsification or after. For example, certain fragrances, colorings, exfoliants, active ingredients, etc., may be added to the aqueous phase, the fatty phase, or after emulsification.

Methods of Use

The instant disclosure also relates to methods of using the cosmetic compositions described herein. For example, the cosmetic compositions can be used in a method that comprises applying the cosmetic compositions to the skin of humans. In some cases, the composition is applied to the face. Furthermore, the cosmetic composition can be used in methods for treating and/or repairing damage to skin (for example, damage from photoaging), and for diminishing the appearance of wrinkles, dark spots, and uneven skin texture of skin. The aforementioned methods are non-therapeutic.

The cosmetic composition may be applied once per day, twice per day, or more than once or twice per day. In some cases, the composition is applied in the evenings before bed. In other cases, the compositions are applies in the morning. In still other cases, the composition may be applied immediately after washing the skin. The compositions may be used once, or for a series of days, weeks, or months. For example, the compositions may be used daily for a period of 1, 2, 3, 4, 5, 6, 7, 8 or more weeks, or months.

Embodiments

In certain embodiments, the cosmetic compositions of the instant disclosure typically include:

about 0.01 to about 3 wt. %, preferably about 0.05 to about 2.5 wt. %; more preferably about 0.1 to about 2 wt. %, of retinol;

about 0.5 to about 10 wt. %, preferably about 0.5 to about 8 wt. %, more preferably about 0.5 to about 5 wt. %, of sodium polyacrylate;

about 0.25 to about 10 wt. %, preferably about 0.25 to about 8 wt. %, more preferably about 0.5 to about 6 wt. % of one or more nonionic emulsifier chosen from polyglyceryl 10-stearate, polyglyceryl-3-caprate, polyglyceryl-3-diisostearate, polyglyceryl-3 methylglucose distearate, and mixtures thereof; and about 3.5 to about 12 wt. %, preferably about 3.5 to about 11 wt. %, more preferably about 3.5 to about 10 wt. %, of a fatty phase, wherein the fatty phase comprises one or more fatty compound including, e.g., fatty alcohols, fatty acids, fatty esters, oils, waxes, derivatives thereof, or a mixture thereof; and water, preferably about 50 to about 90 wt. % of water, more preferably about 60 to about 85 wt. % of water, wherein the cosmetic composition is an oil-in-water emulsion, and all weight percentages are based on the total weight of the cosmetic composition.

In further embodiments, a product is provided comprising:

(i) a cosmetic composition in the form of an oil-in-water emulsion, the cosmetic composition comprising:

about 0.01 to about 3 wt. %, preferably about 0.05 to about 2.5 wt. %; more preferably about 0.1 to about 2 wt. %, of retinol;

about 0.5 to about 10 wt. %, preferably about 0.5 to about 8 wt. %, preferably about 0.5 to about 5 wt. %, of sodium polyacrylate;

about 0.25 to about 10 wt. %, preferably about 0.25 to about 8 wt. %, more preferably about 0.5 to about 6 wt. % of one or more nonionic emulsifier chosen from polyglyceryl 10-stearate, polyglyceryl-3-caprate, polyglyceryl-3-diisostearate, polyglyceryl-3 methylglucose distearate, and mixtures thereof; and about 3.5 to about 12 wt. %, preferably about 3.5 to about 11 wt. %, more preferably about 3.5 to about 10 wt. %, of a fatty phase, wherein the fatty phase comprises one or more fatty compound including, e.g., fatty alcohols, fatty acids, fatty esters, oils, waxes, derivatives thereof, or a mixture thereof;

water, preferably about 50 to about 90 wt. % of water, more preferably about 60 to about 85 wt. % of water, wherein the cosmetic composition is an oil-in-water emulsion, and all weight percentages are based on the total weight of the cosmetic composition; and (ii) a container containing the cosmetic composition including, e.g., non-protective packages, such as those that do not have an aluminum layer and/or have a pump for dispensing the cosmetic composition.

EXAMPLES

The following examples are provided primary for the purpose of elucidating the benefits achieved by embodiments of the disclosure. The examples serve to illustrate the technology without necessarily being limiting in nature.

Example 1

Eight exemplary compositions (Example Formulas A-H) were prepared in accordance with aspects of the disclosure. Example Formulas A-H formed an oil-in-water emulsion. Table 1, shown below, provides the formulation for Example Formulas A-H.

TABLE 1

| | INCI US | Example Formulas A | B | C | D | E | F | G | H | I |
|---|---|---|---|---|---|---|---|---|---|---|
| (a) | RETINOL | 0.2 | 0.3 | 0.2 | 0.2 | 0.2 | 0.2 | 0.2 | 0.2 | 0.2 |
| (b) | SODIUM POLYACRYLATE | 0.6 | 0.6 | 1.3 | 1.3 | 1.3 | 1.3 | 1 | 1.3 | 1.45 |
| (c) | POLYGLYCERYL-3 METHYLGLUCOSE DISTEARATE | 0.4 | 0.4 | 0.8 | 0.8 | 0.8 | 0.8 | 0.8 | 0.8 | 0.75 |
| (d) | CAPRYLIC/CAPRIC TRIGLYCERIDE | 1 | 1 | 1 | 1 | 1 | 1 | 1 | 1 | 1 |
| | ISONONYL ISONONANOATE | 2 | 2 | 2 | 2 | 2 | 2 | 2 | 2 | 3 |
| | GLYCINE SOJA (SOYBEAN) OIL/ GLYCINE SOJA OIL | 1.8 | 2.7 | 1.8 | 1.8 | 1.8 | 1.8 | 1.8 | 1.8 | |
| | ISOHEXADECANE | | | | | | | | | 3 |
| Total Fatty Compounds | | 4.8 | 5.7 | 4.8 | 4.8 | 4.8 | 4.8 | 4.8 | 4.8 | 7 |
| (f) | BUTYLENE GLYCOL | 8 | 8 | 8 | 8 | 8 | 8 | 8 | 8 | 4 |
| | CAPRYLYL GLYCOL | 0.3 | 0.3 | 0.3 | 0.3 | 0.3 | 0.3 | 0.3 | 0.3 | 0.3 |
| | GLYCERIN | 8 | 8 | 8 | 8 | 8 | 8 | 8 | 8 | 8 |
| (g) | ACRYLATES/BEHENETH-25 METHACRYLATE COPOLYMER | 0.2 | 0.2 | 0.2 | 0.2 | 0.2 | 0.2 | 0.2 | 0.2 | 0.5 |
| | METHYL METHACRYLATE CROSSPOLYMER | | | | | | | | 1 | |
| | ALUMINUM STARCH OCTENYLSUCCINATE | 1 | 1 | 1 | | 2 | 3 | 1 | | |
| | PANTHENOL | 0.5 | 0.5 | | | | | 0.5 | | |
| | NIACINAMIDE | 2. | 2 | | | | | 2. | | |
| | SODIUM HYALURONATE | 0.1 | 0.1 | | | | | 0.1 | | 0.2 |
| | TRISODIUM ETHYLENEDIAMINE DISUCCINATE | 0.1 | 0.1 | 0.1 | 0.1 | 0.1 | 0.1 | 0.1 | 0.1 | 0.3 |
| | DIMETHICONE | 0.5 | 0.5 | | | | | 0.5 | | |
| | CHLORPHENESIN | 0.2 | 0.2 | 0.2 | 0.2 | 0.2 | 0.2 | 0.2 | 0.2 | 0.2 |
| | PHENOXYETHANOL | 0.5 | 0.5 | 0.5 | 0.5 | 0.5 | 0.5 | 0.5 | 0.5 | 0.5 |
| | PENTAERYTHRITYL TETRA-DI-T-BUTYL HYDROXYHYDROCINNAMATE | 0.1 | 0.1 | | | | | 0.1 | | |
| | TOCOPHEROL | | | | | | | | | 0.5 |
| (e) | WATER | 72.5 | 71.5 | 74.7 | 75.7 | 73.7 | 72.7 | 71.8 | 74.7 | 74.3 |

Example 2

Example Formulas A-H and eight commercial benchmarks (Comparative Formulas I-P) were stored in a controlled environmental chamber to determine the stability of the retinol over a specified period of time. Example Formulas A-H were not exposed to light during storage in the controlled environmental chamber. The controlled environmental chamber was set to a temperature of 45° C. and a humidity of 50%. Example Formulas A and B were stored in a container that dispenses the composition therein using a standard dropper (in a glass bottle containing a removable lid containing a dropper). Example Formulas C-H were stored in a container that dispenses the composition therein with a standard hand pump.

The retinol concentration of Example Formulas A and B was assessed after 4 weeks, while the retinol concentration of Example Formulas C-H was assessed after 8 weeks of storage. The retinol concentration was determined by analyzing Example Formulas A-H with a HPLC device coupled with UV-Vis. A summary of the results for the assessment of retinol concentration within Example Formulas A-H is provided in Table 2.

TABLE 2

| Example Formula | Pack | % Retinol remaining after storage at 45° C. |
|---|---|---|
| A | Dropper | 100% after 4 weeks (preliminary result) |
| B | Dropper | 100% after 4 weeks (preliminary result) |
| C | Pump | 76% after 8 weeks |
| | Pump | 90% after 8 weeks |
| D | Pump | 78% after 8 weeks |
| E | Pump | 92% after 8 weeks |
| F | Pump | 94% after 8 weeks |
| G | Pump | 90% after 8 weeks |
| H | Pump | 82% after 8 weeks |

Table 3, shown below, provides a summary of the assessment of the retinol concentration for Comparative Formulas I-P.

TABLE 3

| Formula | Formulation | Pack | % Retinol remaining at 8 weeks at 45° C. | Comments |
|---|---|---|---|---|
| I | Commercial Benchmark No. 1 | Jar | 85% | Larger oil phase |
| J | Commercial Benchmark No. 2 | Jar | 69% | Larger oil phase |
| K | Commercial Benchmark No. 3 | Pump | 100% | Larger oil phase |
| L | Commercial Benchmark No. 4 | Aluminum Tube | 46% | Larger oil phase |
| M | Commercial Benchmark No. 5 | Jar | 89% | Larger oil phase |
| N | Commercial Benchmark No. 6 | Jar Pump | 90% 97% | Larger oil phase |
| O | Commercial Benchmark No. 7 | Pump | 0% | Minimal oil phase, poor stability |
| P | Commercial Benchmark No. 8 | Pump Tube | 40% | Minimal oil phase, reduced stability |

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the cosmetic compositions of the instant disclosure can be free or essentially free of all components and elements positively recited throughout the instant disclosure.

In some instances, the cosmetic compositions of the present disclosure may be substantially free of non-incidental amounts of the ingredient(s) or compound(s) described herein. A non-incidental amount of an ingredient or compound is the amount of that ingredient or compound that is added into the cosmetic composition by itself. For example, a cosmetic composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the composition includes both components (or the composition includes more than two components that overlap), an overlapping compound does not represent more than one component. For example, tocopherol may be characterized as both a skin active agent and a preservative. If a particular composition includes both a skin active agent and a preservative, steareth-20 will serve only as the skin active agent or only as the preservative (tocopherol does not serve as both the skin active agent and preservative).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as hair on a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

What is claimed is:

1. A cosmetic composition comprising:

(a) about 0.1 to about 2 wt. % of retinol;

(b) about 0.5 to about 2 wt. % of sodium polyacrylate;

(c) about 0.25 to about 10 wt. % of one or more nonionic emulsifiers selected from polyglyceryl-10-stearate, polyglyceryl-3-caprate, polyglyceryl-3-diisostearate, polyglyceryl-3 methylglucose distearate, and mixtures thereof;

(d) about 3.5 to about 8 wt. % of a fatty phase, wherein the fatty phase comprises one or more fatty compound;

(e) water;

(f) about 1 to about 35 wt. % of one or more water-soluble solvent; and (g) about 0.1 to about 3 wt. % of one or more thickening agents other than sodium polyacrylate, wherein the cosmetic composition is an oil-in-water emulsion, the composition is free from fatty alcohols, the composition does not phase separate and retains at least 90 wt. % of the retinol after storage for 8 weeks at 45° C. in a light-resistant glass container; and all weight percentages are based on the total weight of the cosmetic composition.

2. The cosmetic composition of claim 1, wherein the one or more fatty compound is chosen from fatty alcohols, fatty acids, fatty esters, oils, waxes, derivatives thereof, and mixtures thereof.

3. The cosmetic composition of claim 2 comprising one or more fatty ester chosen from ethoxylated fatty esters, sorbitan fatty esters, esters of stearates, esters of behenates, esters of arachidates, esters of palmitates, fatty acid esters of a sugar, and mixtures thereof.

4. The cosmetic composition of claim 2 comprising one or more fatty ester chosen from purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, and pentaerythritol esters, and mixtures thereof.

5. The cosmetic composition of claim 2, wherein the one or more fatty compounds comprises isononyl isononanoate, caprylic/capric triglyceride, *Glycine soja* (soybean) oil, octyldodecanol, pentaerythritol tetraethylhexanoate, or mixtures thereof.

6. The cosmetic composition of claim 1, wherein the one or more water-soluble solvent is chosen from alkanediols, alcohols, organic solvents, polyols, and mixtures thereof.

7. The cosmetic composition of claim 6, wherein the polyol comprises butylene glycol, caprylyl glycol, or mixtures thereof.

8. The cosmetic composition of claim 6, wherein the alkanediols are chosen from glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol, or a mixture thereof.

9. The cosmetic composition of claim 1, wherein the one or more thickening agent other than sodium polyacrylate is chosen from acrylates, acrylates copolymers, polyacrylamide, carbomer, gums, polysaccharides, and mixtures thereof.

10. The cosmetic composition of claim 1, wherein the one or more thickening agent comprises acrylates/beheneth-25 methacrylate copolymer, methyl methacrylate crosspolymer, or a mixture thereof.

11. A cosmetic product comprising:

(i) a cosmetic composition in the form of an oil-in-water emulsion, the cosmetic composition comprising:

(a) about 0.1 to about 2 wt. % of retinol;

(b) about 0.5 to about 10 wt. % of sodium polyacrylate;

(c) about 0.25 to about 10 wt. % of one or more nonionic emulsifier selected from polyglyceryl-10-stearate, polyglyceryl-3-caprate, polyglyceryl-3-diisostearate, polyglyceryl-3 methylglucose distearate, and mixtures thereof;

(d) about 3.5 to 9 wt. % of a fatty phase, wherein the fatty phase comprises at least one fatty compound;

(e) water;

(f) about 1 to about 35 wt. % of one or more water-soluble solvent; and (g) about 0.1 to about 3 wt. % of one or more thickening agents other than sodium polyacrylate;

wherein the composition does not phase separate and retains at least 90 wt. % of the retinol after storage for 8 weeks at 45° C. in a light-resistant glass container;

the composition is free from fatty alcohols; and all weight percentages are based on the total weight of the cosmetic composition, and (ii) a container containing the cosmetic composition.

12. The cosmetic product of claim 11, wherein the container includes a pump for dispensing the cosmetic composition.

13. The cosmetic product of claim 11, wherein the container does not contain an aluminum layer.

* * * * *